United States Patent [19]

Warriner

[11] Patent Number: Plant 7,221

[45] Date of Patent: Apr. 17, 1990

[54] ROSE PLANT JACRORED

[75] Inventor: William A. Warriner, Tustin, Calif.

[73] Assignee: Jackson & Perkins Company, Medford, Oreg.

[21] Appl. No.: 284,471

[22] Filed: Dec. 14, 1988

[51] Int. Cl.[4] ..... A01H 5/00

[52] U.S. Cl. ..... Plt./20

[58] Field of Search ..... Plt./20, 21

*Primary Examiner*—James R. Feyrer

*Attorney, Agent, or Firm*—Majestic, Parsons, Siebert & Hsue

[57] ABSTRACT

A rose variety of the hybrid tea class is provided that grows vigorously and has a continuous production of large very bright medium red colored flowers with large foliage.

1 Drawing Sheet

SUMMARY OF THE INVENTION

The present invention relates to a new and distinct variety of rose plant of the hybrid tea class, which was originated by me by crossing an unnamed variety with the variety Medallion, U.S. Plant Pat. No. 2,997.

The primary objective of this breeding was to produce a new rose variety of the hybrid tea class displaying bright red color, large flowers and a vigorous plant. This objective was substantially achieved, along with other desirable improvements, as evidenced by the following unique combination of characteristics which are outstanding in the new variety and which distinguish it from its parents as well as from all other varieties of which I am aware. For example, this new rose variety has:

1. A vigorous growth habit to five to five and a half feet tall;
2. Foliage which is quite large, displaying the variety's vigor;
3. Large, bright medium red flowers showing lighter color at petal base and reverse;
4. Thick and leathery petals which last long as cut flowers;
5. Long, heavily appendaged sepals; and
6. A reddish colored rachis.

Asexual reproduction of this new variety by budding, as performed at Wasco, Calif., shows that the foregoing characteristics and distinctions come true to form and are established and transmitted through succeeding propagation.

DESCRIPTION OF THE DRAWING

The accompanying illustration shows typical specimens of the vegetative growth and flowers of this new variety in different stages of development, depicted in color as nearly true as it is reasonably possible to make the same in a color illustration of this character.

DETAILED DESCRIPTION OF THE INVENTION

The following is a detailed description of my new rose variety, which has been denominated "Jacrored". Color terminology is in accordance with The Royal Horticultural Society Colour Chart except where an ordinary dictionary significant for the color is apparent.

Observations of the buds and flowers were made from specimens grown in a greenhouse in October at Somis and Wasco, Calif.

Flower

The blooming habit is continuous. The bud size is one to one and a quarter inches when the petals start to unfurl. The bud form is long with a blunt top. The bud color when sepals first divide is near Red Group 44B. When half blown, the upper side of petals is near Red Group 44A. The lower side of petals is near Red Group 39B. The sepals have a color near Green Group 137C. The surface texture of the sepals is smooth and glabrous. There are three heavily appendaged sepals, and two unappendaged sepals with a hairy edge. The receptacle color is near Green Group 137C and has an apple shape, broad size and smooth surface. The peduncle is long in length and has a glandular surface. Peduncle color is medium green and the peduncle is stiff and erect. The flowers open at a moderate rate and hold open well.

Bloom

Bloom size is medium to large, with an average open size of four to four and one half inches, borne singly. The stems are long in length. The form when first open is high center and is retained to the end but outer petals curl back. Under normal conditions there are 30 to 40 petals. At the center of the flower, the upper side of the petals is near Red Group 45A and the reverse side of the petals at the flower center are near Red Group 39B. Petals have a prominent yellow spot at the base near Yellow Group 8B. The major color is near Red Group 45A. There are no variegations. The general tonality at the end of the first day is very bright, near Red Group 45A. At the end of the third day, the color is still very bright.

There is slight fragrance. The petal texture is thick, leathery and round in shape with a flat form, tips slightly recurved. The arrangement is imbricated with few petaloids in the center. The blooms drop off cleanly, and last both on the plant and as a cut flower for a long time.

Reproductive Parts

The anthers are of large size, of yellow color and arranged regularly around the styles. The filaments are yellow, the pollen is gold yellow, the styles are red, and the stigmas are white.

Plant

The plant has very vigorous, upright branching growth of bush form.

Foliage

The foliage is very large in size and abundant in quantity. New foliage is reddish green in color and old foliage is near Green Group 139A. A normal mid-stem leave has five leaflets.

The leaflets have an oval pointed shape, are smooth and glossy in texture, and have a serrated edge. The serration is single and large. Petiole rachis is reddish, and petiole underside is smooth, with occasional prickles. Stipules are medium and bearded. The foliage is susceptible to mildew under normal growing conditions at Somis and Wasco, Calif.

Wood

New wood is reddish colored with a smooth bark. Old wood is green with a smooth bark.

Prickles

There are an ordinary number of prickles on the main canes from the base and on the laterals from the main canes. The prickles are medium and hooked downward. The prickles are green and red colored when young. There are few small green prickles on the main stalks and on the laterals.

Parentage

The seed parent was of an unnamed variety. The pollen parent was of the variety Medallion.

Classification

Botanical is rosa hybrid. Commercial is hybrid tea.

I claim:

1. A new and distinct variety of rose plant of the hybrid tea class substantially as herein shown and described, characterized particularly as to novelty by the bright medium red flower color with lighter red petal base and reverse, medium-large flower size, excellent plant vigor, long heavily appendaged sepals, distinctive red rachis and thick leathery petals.

* * * * *

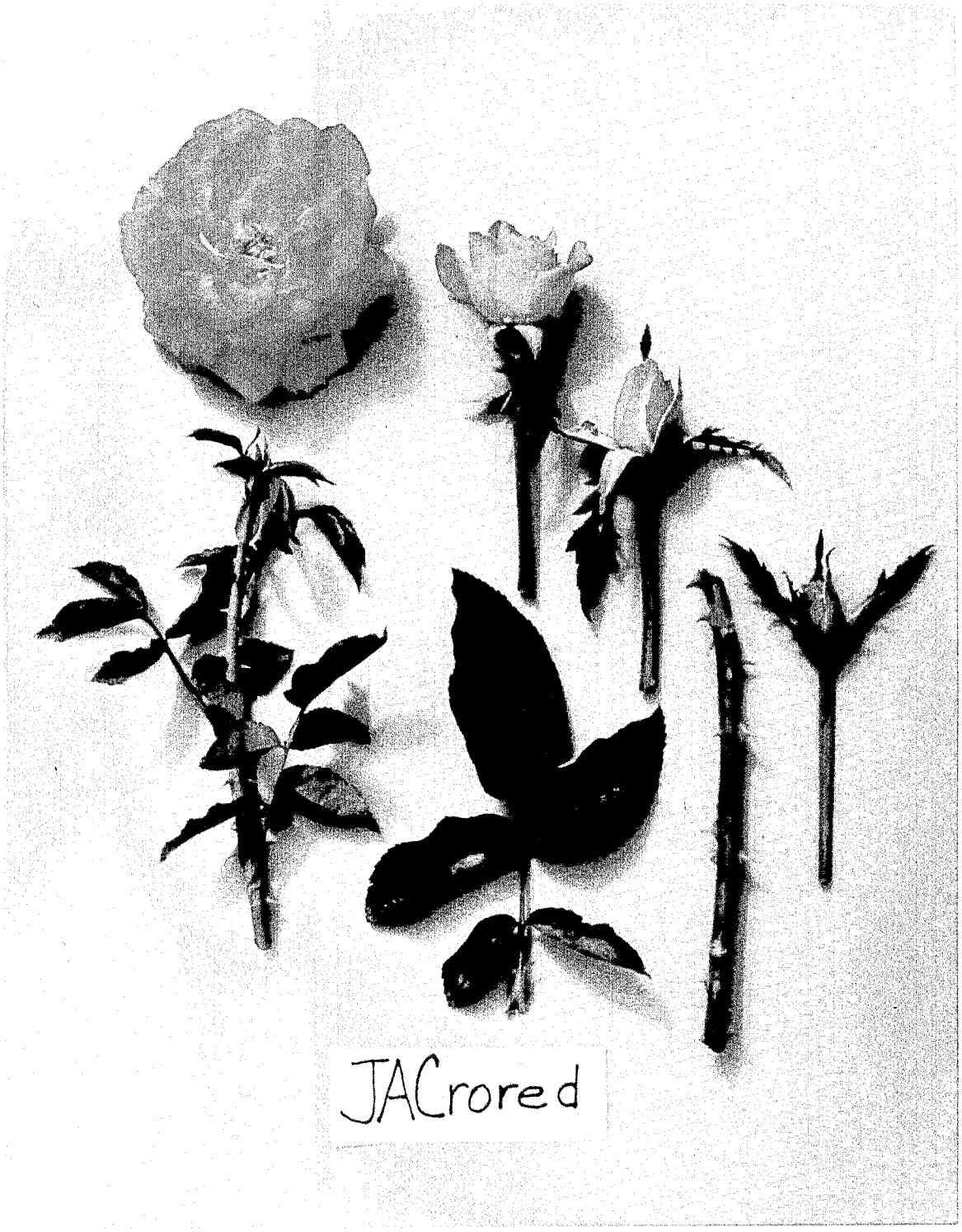
JACrored